United States Patent [19]

Nakamura

[11] 4,320,652

[45] Mar. 23, 1982

[54] INTAKE AIR DENSITY SENSOR FOR AN INTERNAL COMBUSTION ENGINE

[75] Inventor: Koyo Nakamura, Yokosuka, Japan

[73] Assignee: Nissan Motor Co., Ltd., Tokyo, Japan

[21] Appl. No.: 88,553

[22] Filed: Oct. 26, 1979

[30] Foreign Application Priority Data

Nov. 13, 1978 [JP] Japan ................ 53-139667

[51] Int. Cl.³ .............................. G01N 9/32
[52] U.S. Cl. ......................... 73/30; 73/725; 73/729
[58] Field of Search .............. 73/30, 715, 725, 729

[56] References Cited

U.S. PATENT DOCUMENTS

| 2,703,494 | 3/1955 | Carney | 73/30 |
| 2,931,225 | 4/1960 | Pleuger | 73/725 |
| 3,258,966 | 7/1966 | St. Coeur | 73/725 |

FOREIGN PATENT DOCUMENTS 643294 4/1937 Fed. Rep. of Germany ........ 73/725

*Primary Examiner*—Stephen A. Kreitman

*Attorney, Agent, or Firm*—Lane, Aitken, Kice & Kananen

[57] ABSTRACT

An intake air density sensor for an internal combustion engine comprises a receptacle in the form of a flask including a spherical chamber and a tubular portion having a very fine diameter, a pressure responsive casing at least whose part is made of an elastomeric membrane and communicated with the receptacle, a gas and a conductive liquid hermetically sealed in the receptacle and pressure responsive casing, respectively, so as to locate a boundary surface between the gas and liquid in the tubular portion, and a resistor longitudinally arranged in the tubular portion so as to form short-circuiting means by the conductive liquid for the resistor, thereby detecting densities of a fluid to be measured by converting variations in pressure of fluid into variations in volume of the pressure responsive casing or sealed gas and further converting variations in position of the boundary surface of the conductive liquid into values of electrical resistances of the resistor without affecting the positional movement of the boundary surface to convert variations in density of the fluid into electrical signals with high detecting sensitivities and high accuracies.

8 Claims, 11 Drawing Figures

FIG.3 FIG.4 FIG.5
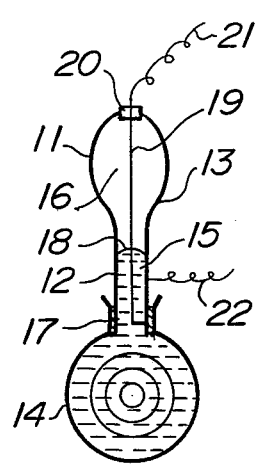
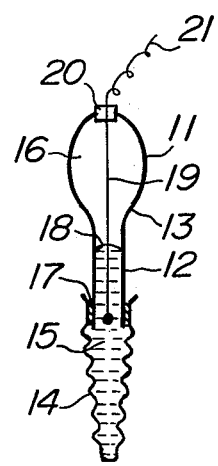
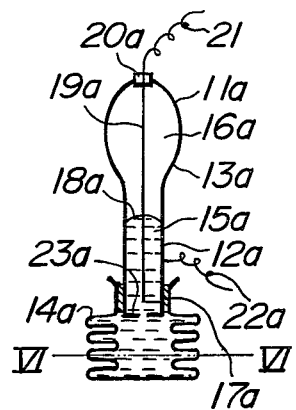
FIG.6 FIG.7 FIG.8
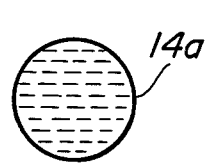
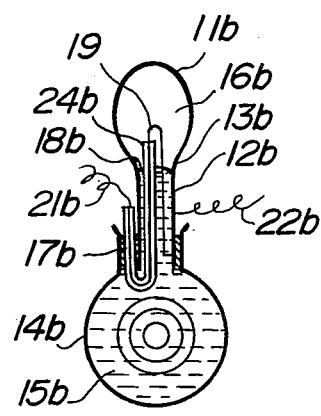
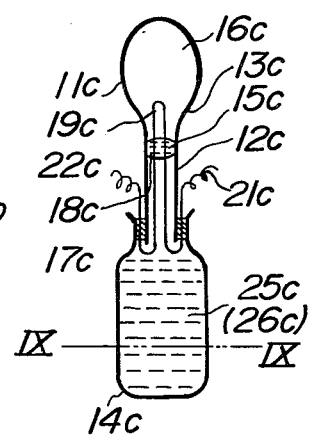
FIG.9

INTAKE AIR DENSITY SENSOR FOR AN INTERNAL COMBUSTION ENGINE

BACKGROUND OF THE INVENTION

1. Field of the Invention

The present invention relates to an intake air density sensor, and more particularly to an intake air density sensor for an internal combustion engine with an electronically controlled fuel injection system which is required to control the fuel injection correspondingly to the intake air mass flow and therefore required to convert signals obtained from a volumetric flow detector such as the Karman vortices flow meter generally used in detecting the intake air flow into signals exactly corresponding to the intake air mass flows.

2. Description of the Prior Art

When a determined amount of a gas enclosed in a vessel is kept under the same pressure at the same temperature as those of a fluid to be measured, the volume of the gas changes proportionally to variations in pressure and temperature. Accordingly, a density of the fluid to be measured can be determined in a reciprocal by measuring the volume of the gas enclosed in the vessel under the above condition.

In density sensors of prior art according to such a principle, a gas is hermetically sealed in a vessel made of a rubber diaphragm, metal bellows or aneroid barometer vessel which deforms to equalize pressures in and out thereof. The deformation of the vessel is converted into a movement of a slider of a potentiometer to detect the variation in volume of the sealed gas and hence the variation in density of the fluid to be measured. Such density sensors have encountered various problems in elastic restoration of the diaphragm or bellows, resistance to the deformation, frictional resistance of sliding portions, inclination of the slider of the potentiometer or the like, which would cause errors in measurements. Accordingly, it has been difficult to detect in a high sensitivity the delicate variation in density of the fluid, if not impossible, and the devices are very sophisticated in construction and expensive to manufacture.

SUMMARY OF THE INVENTION

It is an object of this invention to provide an improved air density sensor which eliminates all the disadvantages of the prior art above described.

It is further object of this invention to provide an intake air density sensor for an internal combustion engine, which is inexpensive to manufacture and detects in a high sensitivity with a high accuracy a density of the intake air.

It is another object of this invention to provide an intake air density sensor for an internal combustion engine, which comprises a receptacle in the form of a flask including a spherical chamber and a tubular portion having a very small diameter, a pressure responsive casing communicating with the receptacle, and a liquid and a gas hermetically sealed in the pressure responsive casing and receptacle, respectively, so as to locate a boundary surface between the liquid and gas in the tubular portion, thereby utilizing the boundary surface displaceable in high sensitivity correspondingly to variations in volume of the pressure responsive casing and hence gas therein to convert the position of the boundary surface into electrical signals without affecting the displacement of the boundary surface and thereby measuring variations in volume of the gas to detect variations in density of the fluid to be measured, without directly detecting deformations of the pressure responsive casing whose volume changes.

The invention will be more fully understood by referring to the following detailed specification and claims taken in connection with the appended drawings.

BRIEF DESCRIPTION OF THE DRAWINGS

FIG. 2a is a front elevation of the density sensor shown in FIG. 1 with a mounting plate and a bracket;

FIG. 2b is a side view of the density sensor shown in FIG. 2a;

FIG. 2c is a top plan view of the density sensor shown in FIG. 2a;

FIG 3 is a sectional view of a density sensor of a first embodiment of the invention;

FIG. 4 is a sectional side view of the density sensor shown in FIG. 3;

FIG. 5 is a sectional view of a density sensor of a second embodiment of the invention;

FIG. 6 is a sectional view of the sensor taken along the line VI—VI in FIG. 5;

FIG. 7 is a sectional view of a density sensor of a third embodiment of the invention;

FIG. 8 is a sectional view of a density sensor of a fourth embodiment of the invention; and FIG. 9 is a sectional view of the sensor taken along the line IX—IX in FIG. 8.

DETAILED DESCRIPTION OF THE PREFERRED EMBODIMENT

Figure 1:
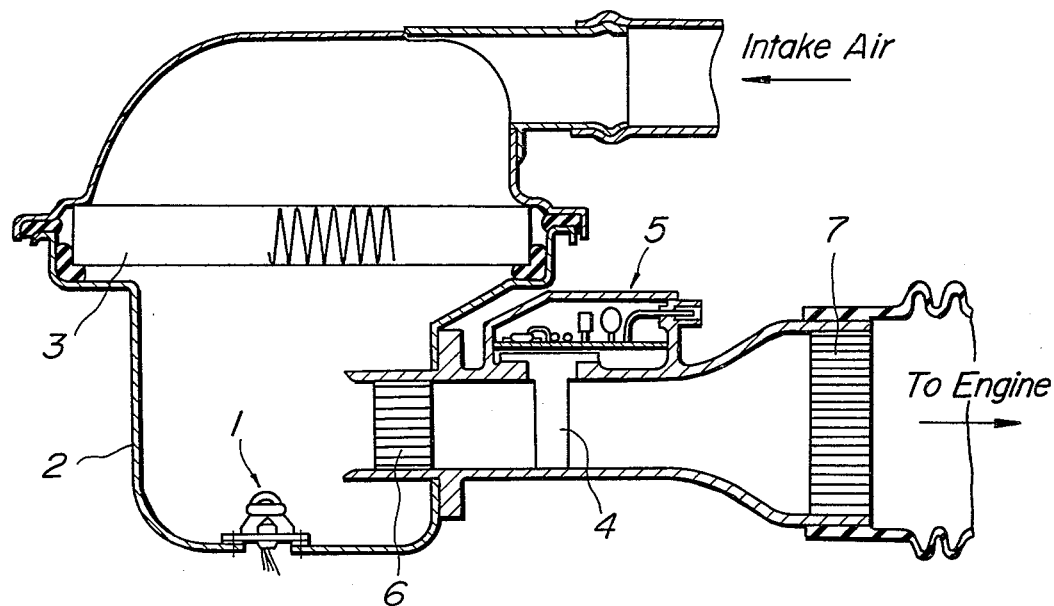
FIG. 1 is a sectional view of a part of an internal combustion engine including an air cleaner and a Karman vortices flow meter for illustrating the arrangement of an intake air density sensor according to the invention mounted in the engine.

FIG. 1 and FIGS. 2a–2c illustrate how an intake air density sensor according to the invention is installed in a part of an internal combustion engine. As can be seen from FIG. 1, the sensor 1 is mounted on an inside of a casing 2 of an air cleaner downstream of an air cleaner element 3. An air passage downstream of the air cleaner includes a Karman vortices flow meter comprising vortices generating means 4, a Karman signal treatment device 5 and flow rectifiers 6 and 7 in the form of honeycombs.

Figures 2A, 2B:
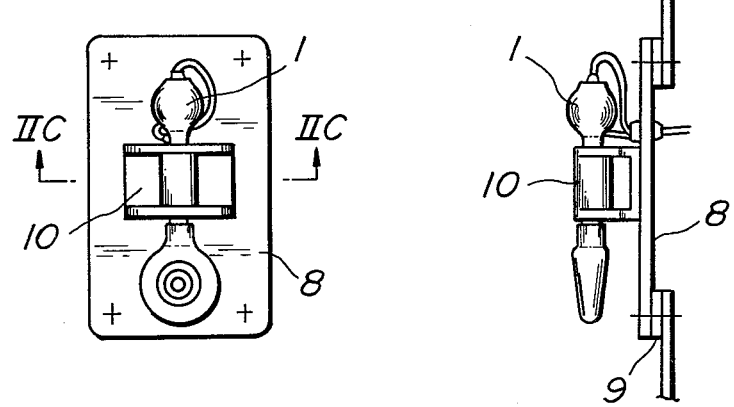
Figure 2C:
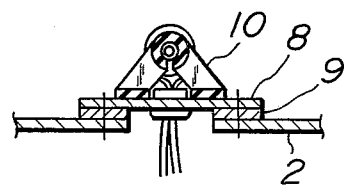

Referring to FIGS. 2a–2c, a mounting plate 8 is secured to the casing 2 of the air cleaner with a gasket 9 therebetween about an opening of the casing for lead wires of the density sensor 1. On the mounting plate 8 is supported the density sensor 1 by means of a bracket 10 made of a soft rubber which serves to absorb vibrations.

Referring to FIGS. 3 and 4 illustrating a first embodiment of the invention, the intake air density sensor comprises a metal receptacle 13 in the form of a flask including a spherical chamber 11 and a tubular portion 12 having a very small diameter, and a disk-like pressure responsive casing 14 communicating through an opening end of the tubular portion 12 with the metal receptacle 13. In a used position, the density sensor is in its vertical position with the receptacle above the pressure responsive casing. The pressure responsive casing 14 is made of an elastomeric membrane such as a soft rubber having concentric pleats or corrugations such that the volume of the casing 14 is freely changeable in response to a difference between pressures in and out of the casing 14 until they equalize to each other. The receptacle 13 may be made of an electric insulator having a high thermal conductivity whose inner surface is metal-plated.

The receptacle 13 and pressure responsive casing 14 are filled with a gas 16 and an electric conductive liquid 15 such as mercury, electrolyte or the like and hermetically sealed by a sealing material 17 applied to a fitted portion of the receptacle 13 and casing 14. In this case, the relative positional arrangement of the two receptacles 13 and 14 and volumes of the receptacles, gas 16 and liquid 15 are so selected that the conductive liquid 15 is in the pressure responsive casing 14 and the gas 16 in the casing 13, and the boundary surface 18 between the liquid 15 and gas 16 is situated substantially at the center of the tubular portion 12.

A bare resistance wire 19 whose one end is directly connected to the lower end of the receptacle 13 extends vertically along its center line without contacting its any remaining portion and the other end of the wire 19 extends out of the receptacle 13 through a center of an insulator 20 fitted in the apex thereof. The insulator 20 has an electric resistance remarkably greater than those of the conductive liquid 5 and receptacle 3. To the other end of the resistance wire 19 extending out of the receptacle 13 is connected a lead wire 21, and to the receptacle 13 is connected a lead wire 22. In case of the receptacle 13 having inner metal-plated surfaces, the lead wire 22 is directly connected to the metal-plate layer.

With this arrangement, as the values of electrical resistances of the conductive liquid 15 and receptacle 13 are negligible in comparision with that of the resistance wire 19, that portion of the wire 19 immersed in the conductive liquid 15 is short-circuited, so that the electrical resistance between the lead wires 21 and 22 is substantially equal to the resistance of that part of the wire 19 between a connection to the lead wire 21 and the boundary surface 18, which depends upon the volume of the gas 16.

When the air density sensor is arranged in a fluid to be measured, the pressure responsive casing 14 deforms immediately so as to change the volume therein until the pressures in the conductive liquid 15 and gas 16 hermetically sealed in the receptacle 13 and the pressure responsive casing 14 respectively become substantially equal to the pressure in the fluid to be measured, and simultaneously the volume of the gas 16, therefore, changes in response to the deformation of the casing 14, so that the boundary surface 18 moves correspondingly.

At this time, as the internal sectional area of the tubular portion 12 is very small such that the volume change of the pressure responsive casing 14 or gas 16 is indicated in an exaggerated scale in a very sensitive movement of the boundary surface 18.

On the other hand, the temperature of the gas 16 becomes immediately equal to that of the fluid to be measured through the metal receptacle 13 having the high thermal conductivity, so that the density of the gas 16 becomes equal to that of the fluid to be measured simultaneously.

Moreover, the density of the gas 16 is in reverse proportional to the volume thereof, so that the electrical resistance between the lead wires 21 and 22 changes depending upon the density of the fluid to be measured. Accordingly, the density of the fluid to be measured can be determined from the electrical resistance between the lead wires 21 and 22 in the relation that the smaller the density, the larger is the resistance. At the time, the movement of the boundary surface 18 is not affected by the resistor 19.

The sensitivity of the density sensor becomes higher as the volume of the gas 16 is larger, the inner sectional area of the tubular portion 12 smaller and the deformation resistance of the pressure responsive casing 14 smaller. Accordingly, the volume of the gas 16 and constructions of the tubular portion 12 and pressure responsive casing 14 are particularly important.

Referring to FIGS. 5 and 6 illustrating the second embodiment of the invention wherein the same reference numerals followed by the letter "a" have been utilized to identify like part, a pressure responsive casing 4a is composed of disc-like casings piled in the form of bellows and an orifice 23a is provided in an opening end of a receptacle 13a to prevent a conductive liquid 15a in the pressure responsive casing 14a from being violently forced into and out of the receptacle 13a due to vibrations, thereby stabilizing movements of a boundary surface 18a and hence the detecting performance of the sensor. The other construction and operation are the same as those of the first embodiment of the invention shown in FIGS. 3 and 4.

FIG. 7 illustrates a third embodiment of the invention, the same reference numerals followed by the letter "b" have been utilized to identify like part. In this embodiment, a resistance wire 19 is not extended from an apex of a receptacle 13b but is bent downwardly and again bent upwardly to form a doubled portion which is covered by an insulator 24b and extends out of the receptacle 13b through a fitted portion of the receptacle 13b and casing 14b to simplify the construction of the receptacle 13b. The other construction and operation of this embodiment are the similar to those of the first embodiment shown in FIGS. 3 and 4.

Referring to FIGS. 8 and 9 illustrating a fourth embodiment of the invention, the same reference numerals followed by the letter "c" have been utilized to identify like part. A receptacle 13c in the form of a flask made of an insulating material or metal having a high thermal conductivity is fitted in an elliptical pressure responsive casing 14c to communicate with each other. The receptacle 13c and pressure responsive casing 14c are filled with a gas 16c and a nonconductive liquid 25c having a light specific gravity together with a small amount of a conductive liquid 15c and hermetically sealed therein to form a thin film of the conductive liquid 15c between the gas 16c and liquid 25c in a tubular portion 12c of the receptacle 13c. Although the specific gravity of the conductive liquid 15c is more than that of the nonconductive liquid 25c, the liquid 15c remains above the nonconductive liquid 25c because the diameter of the tubular portion 12c of the receptacle 11c is so small, for example, 1 millimeter to exhibit a capilarity which retains the heavier liquid 15c over the nonconductive liquid 25c. As above described, the density sensor is generally arranged in a vertical position with the receptacle enclosing the gas above the pressure responsive casing enclosing the liquid.

A resistance wire 19c is bent into an inverted U-shaped wire which extends along a center line of the tubular portion 12c through the conductive liquid 15c. Lower ends of the U-shaped wire extend out of the receptacle 13c and pressure responsive casing 14c through a fitted portion thereof.

As that portion of the resistance wire 19c above a boundary surface 18c of the conductive liquid 15c is short-circuited by the boundary surface 18c, the value of electrical resistance of the resistance wire 19c between lead wires 21c and 22c changes dependently upon the position of the film of the conductive liquid 15c or the volume or density of the gas 16c.

Instead of the liquid 25c a gas the same as or different from the gas 16c may be used.

With the density sensor of this embodiment, the receptacle 13c is not necessarily metal and may be electrically insulating material and the inside of the receptacle 13c is not necessarily metal-plated, so that the construction of the receptacle 13c is very simplified. Moreover, with the sensor of this embodiment, the weights of the conductive liquid 15c and liquid 25c scarcely interfere with the deformation of the pressure responsive casing 14c because of the small amount of the conductive liquid 15c and light weight of the liquid 25c, which serve to keep at a high level the detecting sensitivity of the sensor.

Other construction and operation of the sensor of this embodiment are substantially similar to those of the first embodiment shown in FIGS. 1 and 2.

As can be seen from the above description, the density sensor according to the invention is simple in construction and inexpensive to manufacture and detects densities of a fluid to be measured by converting variations in pressure of the fluid to be measured into variations in volume of the pressure responsive casing 14, 14a, 14b or 14c or the sealed gas 16, 16a, 16b or 16c without directly measuring the deformation of the pressure responsive casing, and further converting variations in position of the boundary surface 18, 18a, 18b or 18c of the conductive liquid very sensitively movable in response to the volumetric variation into values of electrical resistances of the resistor 19, 19a, 19b or 19c without affecting the positional movement of the boundary surface to convert variations in density of the fluid to be measured into electrical signals with high detecting sensitivities and high accuracies.

It is further understood by those skilled in the art that the foregoing description is preferred embodiments of the disclosed sensors and that various changes and modifications may be made in the invention without departing from the spirit and scope thereof.

What is claimed is:

1. An air density sensor comprising:
    a high thermal conductivity receptacle having a fine diameter tubular portion;
    a pressure responsive casing at least whose part is made of an elastic membrane and communicated with said receptacle;
    a gas and a nonconductive liquid having a light specific gravity together with a small amount of a conductive liquid and hermetically sealed in said receptacle and pressure responsive casing to form a thin film of the conductive liquid between the gas and nonconductive liquid in the tubular portion of said receptacle; and
    a resistor longitudinally arranged in said tubular portion so as to form short-circuiting means by said conductive liquid for said resistor, whereby values of electrical resistance between ends of said resistor vary with movements of said thin film of said conductive liquid in response to outer pressures and temperatures.

2. An air density sensor as set forth in claim 1, wherein instead of said nonconductive liquid a gas the same as said gas in the receptacle is used.

3. An air density sensor as set forth in claim 1, wherein instead of said nonconductive liquid a gas different from said gas in the receptacle is used.

4. An air density sensor as set forth in claim 1, wherein said resistor is bent into an inverted U-shaped form which extends through said conductive liquid and has lower ends that extend out of said receptacle and pressure responsive casing through a fitted portion thereof.

5. An air density sensor comprising:
    a receptacle of high thermal conductivity having a fine diameter tubular portion in communication with a pressure responsive casing that has a portion thereof made from an elastomer membrane, said receptacle and pressure responsive casing containing a gas, a nonconductive liquid of light specific gravity, and a small amount of conductive liquid hermetically sealed therein to form a thin film of conductive liquid between the gas and the nonconductive liquid in said tubular portion, and resistance means longitudinally arranged in said tubular portion so as to be short circuited by said conductive liquid, whereby the electrical resistance of said resistance means varies with movement of said conductive liquid in said tubular portion in response to outer pressures and temperatures.

6. An air density sensor as set forth in claim 5, wherein said resistor is bent into an inverted U-shaped form which extends through said conductive liquid and has lower ends that extend out of said receptacle and pressure responsive casing through a fitted portion thereof.

7. The air density sensor as set forth in claim 5 wherein instead of said nonconductive liquid, a gas the same as the gas in said receptacle is used.

8. The air density sensor as set forth in claim 5 wherein instead of said nonconductive liquid a gas different from the gas in the receptacle is used.

* * * * *